United States Patent [19]

Feld et al.

[11] Patent Number: 5,097,030
[45] Date of Patent: Mar. 17, 1992

[54] PROCESS FOR THE PREPARATION OF 2-(METHYLTHIO)BARBITURIC ACID

[75] Inventors: Marcel Feld, Cologne; Friedrich Goerentz, Niederkassel, both of Fed. Rep. of Germany

[73] Assignee: Huels Aktiengesellschaft, Marl, Fed. Rep. of Germany

[21] Appl. No.: 559,635

[22] Filed: Jul. 30, 1990

[30] Foreign Application Priority Data

May 3, 1990 [DE] Fed. Rep. of Germany ....... 3925687

[51] Int. Cl.$^5$ ........................................... C07D 239/02
[52] U.S. Cl. ................................................... 544/299
[58] Field of Search ......................................... 544/299

[56] References Cited

U.S. PATENT DOCUMENTS

| 2,140,987 | 12/1938 | Dickey | 544/299 |
| 2,161,212 | 6/1939 | Whitmore | 544/299 |
| 2,876,225 | 3/1959 | Donnison | 544/299 |
| 4,199,583 | 4/1980 | Moon et al. | 514/274 |

OTHER PUBLICATIONS

Moon et al., CA 93-90184k (1980).
Muehle et al., CA 82-4292n (1975).
Maurer et al., CA 86-140080b (1977).

*Primary Examiner*—Cecilia Shen
*Attorney, Agent, or Firm*—Felfe & Lynch

[57] ABSTRACT

2-(methylthio)barbituric acid is obtained with high yields and degree of purity by reacting a solution or suspension of an alkali metal salt or alkaline earth metal salt of 2-thiobarbituric acid with methyl bromide at a pressure of 1.5 to 5 bar.

2 Claims, No Drawings

PROCESS FOR THE PREPARATION OF 2-(METHYLTHIO)BARBITURIC ACID

FIELD OF THE INVENTION

This invention relates to a novel process for the preparation of 2-(methylthio)barbituric acid, which is useful as an intermediate in the preparation of plant protection agents, for example.

The preparation of 2-(methylthio)barbituric acid pursuant to the present invention comprises reacting an aqueous solution or suspension of the sodium salt of 2-thiobarbituric acid with methyl bromide at mildly elevated temperatures below 90° C. and under an increased pressure of 1.5 to 5 bar.

BACKGROUND OF THE INVENTION

The preparation of 2-(methylthio)barbituric acid by methylation of the sodium salt of 2-thiobarbituric acid is described in the prior art. The methylating reagents used in the prior art are dimethyl sulfate (German Offenlegungsschrift 2,412,854, Example 12; and German Offenlegungsschrift 2,523,324, Example c), or methyl iodide (U.S. Patent No. 4,199,583). Despite the use of these particularly reactive alkylating agents, the yields of 2-(methylthio)barbituric acid remained unsatisfactory (33% in German Offenlegungsschrift 2,523,324; and 89.3% in U.S. Pat. No. 4,199,583), and the product was of insufficient purity. Moreover, dimethyl sulfate and methyl iodide are toxic substances and therefore require extensive safety precautions.

OBJECTS OF THE INVENTION

It is an object of the present invention to provide a process for the preparation of 2-(methylthio)barbituric acid which produces the target product with satisfactory yields and high purity, and at the same time avoids the use of dimethyl sulfate or methyl iodide.

Other objects and advantages of the present invention will become apparent as the description thereof proceeds. cl DESCRIPTION OF THE INVENTION The above object is achieved in accordance with the present invention by the use of methyl bromide for the methylation of 2-thiobarbituric acid.

We have discovered that an aqueous solution of the sodium salt of thiobarbituric acid can be efficiently reacted with methyl bromide even at mildly elevated temperatures. This discovery was surprising in view of the results achieved in the above described prior art processes, where the particularly effective methylating agents dimethyl sulfate and methyl iodide were used. In the process according to the present invention it has proved to be important to maintain a relatively narrow temperature range under increased pressure in order to obtain a high yield and high purity of the target product.

We have been able to show that 2-(methylthio)barbituric acid decomposes in the presence of water at temperatures above 80° C. to a substantial extent and forms methyl mercaptan. This decomposition reaction not only results in yield losses and contamination of the product, but also raises problems because of the unpleasant odor.

On the other hand, as expected, the rate of reaction of an aqueous sodium thiobarbiturate solution with methyl bromide under atmospheric pressure and mildly elevated temperatures is too slow for the preparation of 2-(methylthio)barbituric acid on an industrial scale.

The present invention, therefore, is based on the observation that the rate of reaction of an aqueous solution or suspension of an alkali metal salt or an alkaline earth metal salt of 2-thiobarbituric acid with methyl bromide at mild temperatures, such as room temperature, is increased to a surprisingly large extent by only slightly increasing the pressure, for example to that corresponding to the vapor pressure of methyl bromide at these mild temperatures.

Accordingly, the process of the present invention for the preparation of 2-(methylthio)barbituric acid comprises reacting an aqueous solution and/or suspension of an alkali metal salt and/or an alkaline earth metal salt of 2-thiobarbituric acid at temperatures of 20° to 80° C., preferably 20° to 60° C., and at an increased pressure of 1.5 to 5 bar. The preferred pressure is the vapor pressure of methyl bromide.

The process of the instant invention makes it possible to prepare 2-(methylthio)barbituric acid under simple operational conditions and in reaction periods of less than 10 hours with high purity of more than 99% and high yields of more than 90% of theory. After the reaction has gone to completion, 2(methylthio)barbituric acid, which is virtually insoluble in water, only needs to be separated from the liquid phase by a conventional solid/liquid separation procedure.

To avoid decomposition of the target product during drying at elevated temperatures, it is advantageous to displace at least most of the water contained in the filter-moist product before drying by a suitable solvent or solvent mixture. Acetone is an example for a solvent which has proved to be suitable for this purpose.

Of course, the aqueous solution or suspension of thiobarbituric acid salts which is employed in the process of the present invention may also contain other solvents which are miscible with water or, depending on their solubility, partially miscible with water. For example, it is possible according to processes known from the prior art that sodium thiobarbiturate which is prepared by reacting thiourea, diethyl malonate and sodium ethanolate and which is separated from an ethanolic suspension, may be employed without previous drying, together with the ethanol contained in the filter-moist product, for the methylation according to the invention to produce 2(methylthio)barbituric acid in an aqueous medium which then necessarily contains ethanol.

The methylation reaction according to the present invention is performed while agitating the solution or suspension either by stirring or circulation pumping. The methyl bromide can be introduced into the reaction vessel in the liquid or the gaseous state. If the methyl bromide is introduced in the gaseous state, it may be fed directly into the solution or suspension or also into the vapor phase above the solution or suspension, followed by increase in the pressure to the required value.

The rate of reaction of sodium thiobarbiturate with methyl bromide and the solubility of the salt as well as that of the desired end product in the aqueous medium can be increased by the presence of excess alkali. In that event, 2-(methylthio)barbituric acid is precipitated after completion of the reaction by adding an amount of a suitable acid which corresponds to the excess of alkali. On the other hand, the presence of excess alkali is of disadvantage with regard to the purity of 2-(methylthio)barbituric acid inasmuch as dimethylated thiobarbituric acid derivatives are also formed in small amounts under these conditions. If these slight impurities do not impair subsequent reactions, the methylation according to the present invention can also be performed in the presence of a stoichiometric excess of base relative to the thiobarbituric acid reactant, for example an excess of up to about 3 equivalents. However, if 2-(methylthio)barbituric acid of high purity is desired, an excess of base is to be avoided by using either a thiobarbituric acid salt as such or alternatively thiobarbituric acid with an equivalent amount of a base.

The following examples illustrate the present invention and will enable others skilled in the art to understand it more completely. It should be understood, however, that the invention is not limited solely to the particular examples given below.

EXAMPLE 1

A reaction vessel containing 20 g of sodium thiobarbiturate and 100 g of water was connected to a pressurized vessel containing methyl bromide, so that a pressure of 1.9 bar was established in the reaction vessel. While stirring, the contents of the reaction vessel were heated to 45° C., and, while maintaining the pressure and temperature, the reaction was allowed to proceed over a period of 8 hours during which more and more 2-(methylthio)barbituric acid precipitated in the form of a white crystallizate. After the reaction had gone to completion the solid product which had formed was filtered off, washed with water and acetone and was then dried in vacuo at a temperature which was gradually increased to 100° C. 17.4 g (91.3% of theory) of 2-(methylthio)barbituric acid with a purity of 99.8% were obtained.

EXAMPLE 2

Example 1 was repeated, but 23.4 g of sodium thiobarbiturate were used which had been prepared by reacting thiourea with diethyl malonate and sodium ethanolate in ethanol and which still contained 2.3 g of ethanol. After a reaction time of 4 hours, 18.6 g (92.7% of theory) of 2-(methylthio)barbituric acid of the same purity as in Example 1 were obtained.

EXAMPLE 3

Example 1 was repeated, except that the reaction was performed at 70° C. and over a reaction period of 4 hours. 16 g (84% of theory) of 2-(methylthio)barbituric acid with a purity of 99.2% were obtained. Significant odor problems were encountered during the reaction product's recovery.

Comparison Examples A and B

Example 1 was repeated at a reaction temperature of 90° C. and for a reaction period of (A) 2 hours and (B) 6 hours, respectively. The yield of crude 2-(methylthio)barbituric acid was (A) 3.6 g and (B) 14.7 g with purities of only 33.4% and 44%, respectively.

EXAMPLE 4

Example 1 was repeated, except that the reaction temperature was 20° C. and the reaction was allowed to proceed for 8 hours. 11.9 g (62.5% of theory) of 2-(methylthio)barbituric acid with a purity of 99.8% were obtained.

EXAMPLE 5

Example 1 was repeated, except that the reaction temperature was 25° C. and the reaction was allowed to proceed for 16 hours. 17.7 g (93% of theory) of 2-(methylthio)barbituric acid with a purity of 99.8% were obtained.

EXAMPLE 6

Example 1 was repeated at a reaction temperature of 20 to 25° C. and a reaction time of 24 hours, using 20 g of sodium thiobarbiturate, 90 g of water and 15 g of methanol. 17 g (89.5% of theory) of 2-(methylthio)barbituric acid with an acceptable purity were obtained.

EXAMPLE 7

Example 4 was repeated with 17.3 g (0.12 mol) of 2-thiobarbituric acid, 9.6 g of sodium hydroxide (0.24 mol) and 100 g of water. After only 4 hours of reaction time the reaction mixture was acidified with sulfuric acid and yielded 15.5 g (82% of theory) of 2-(methylthio)barbituric acid with a purity of 95.7%.

Comparison Example C

A clear solution of 16.6 g of sodium thiobarbiturate in 200 g of water was charged into a round-bottom flask, and then the air above the liquid phase was replaced by evacuation and introduction of methyl bromide. The reaction mixture was then stirred vigorously at 20° to 25° C. under atmospheric pressure. To compensate for any losses of methyl bromide due to possible reactions in the gaseous phase, a constant supply of methyl bromide under atmospheric pressure was provided. After 19 hours, a weight increase of less than 1 g was observed in comparison with the evacuated flask. The slightly turbid solution contained no product which could be isolated by filtration and had a bromine content of only 629 mg (=7.9% of theory).

EXAMPLE 8

After completion of the reaction described in Comparison Example C, the methyl bromide pressure in the gas phase above the slightly turbid solution obtained after 19 hours was increased to 1.9 bar, and the run was continued under this increased pressure for 4 hours under otherwise identical conditions. After only 30 minutes, precipitation began and increased further as the reaction proceeded. The run was stopped after 5 hours. Filtration yielded 12.4 g (78% of theory) of 2-(methylthio)barbituric acid, and the bromine content in the filtrate was 7.06 g (=88% of theory).

EXAMPLE 9

A suspension of 14.2 g of 2-thiobarbituric acid (0.1 mol) and 2.9 g of calcium oxide (0.05 mol) in 200 g of water was treated with methyl bromide for 20 hours as described in Example 1. After the pressure in the vessel was released, an increase in weight of the suspension of 12.0 g, corresponding to a methyl bromide uptake of 0.13 mol, was determined. Filtration and drying of the filter cake yielded 13.4 g of 2-(methylthio)barbituric acid with a purity of 96.9% (83.3% of theory).

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing 2-(methylthio)barbituric acid which comprises reacting an aqueous solution or suspension of an alkali metal salt or an alkaline earth metal salt of 2-thiobarbituric acid with methyl bromide at a temperature between room temperature and 80° C. and under an elevated pressure of 1.5 to 5 bar.

2. The method of claim 1, wherein the reaction is performed at a temperature of 20° to 60° C.

* * * * *

UNITED STATES PATENT AND TRADEMARK OFFICE
CERTIFICATE OF CORRECTION

PATENT NO.   : 5,097,030

DATED        : March 17, 1992

INVENTOR(S)  : Marcel Feld et al

It is certified that error appears in the above-identified patent and that said Letters Patent is hereby corrected as shown below:

Title page (30), "May 3, 1990" should read --August 3, 1989--.

Column 1, line 43, delete "cl".

Signed and Sealed this

Twenty-first Day of September, 1993

Attest:

BRUCE LEHMAN

Attesting Officer       Commissioner of Patents and Trademarks